United States Patent [19]

Hagiwara

[11] Patent Number: 5,468,452
[45] Date of Patent: Nov. 21, 1995

[54] QUANTITATIVE ANALYSIS COMBINING HIGH PERFORMANCE LIQUID CHROMATOGRAPH AND MASS SPECTROMETER

[76] Inventor: Teruhiko Hagiwara, 26-19, Kitahara-cho 1-chome, Tanashi-shi, Tokyo 188, Japan

[21] Appl. No.: 300,319

[22] Filed: Sep. 2, 1994

[30] Foreign Application Priority Data

Jun. 14, 1994 [JP] Japan .................................. 6-131968

[51] Int. Cl.⁶ ................................................ G01N 30/02
[52] U.S. Cl. .......................... 422/70; 73/61.61; 250/288
[58] Field of Search ................... 422/70, 907; 73/61.61; 210/198.2; 250/281, 288

[56] References Cited

U.S. PATENT DOCUMENTS

| | | | |
|---|---|---|---|
| 3,845,307 | 10/1974 | Gallo ...................................... | 250/326 |
| 4,112,297 | 9/1978 | Miyagi et al. ........................... | 250/288 |
| 4,769,540 | 9/1988 | Mitsui et al. ............................ | 250/288 |
| 4,839,143 | 6/1989 | Vora et al. ................................ | 422/98 |
| 4,888,482 | 12/1989 | Kato ........................................ | 250/281 |
| 4,982,097 | 1/1991 | Slivon et al. ............................ | 250/281 |
| 4,996,424 | 2/1991 | Mimura et al. .......................... | 250/288 |

Primary Examiner—James C. Housel
Assistant Examiner—Jan M. Ludlow
Attorney, Agent, or Firm—Parkhurst, Wendel & Rossi

[57] ABSTRACT

A quantitative analyzing apparatus including a high-performance liquid chromatograph, a mass spectrometer, and an atmospheric pressure chemical ionization interface for linking the liquid chromatograph to the mass spectrometer to each other, wherein the interface includes an ionization chamber housing a corona discharge electrode. According to the present invention the electrode is comprised of a material selected from the group consisting of a silver alloy and a non-plated iron, and thereby quantitative analysis of organic compounds may be carried out.

4 Claims, 1 Drawing Sheet

QUANTITATIVE ANALYSIS COMBINING HIGH PERFORMANCE LIQUID CHROMATOGRAPH AND MASS SPECTROMETER

BACKGROUND OF THE INVENTION

The present invention relates to a quantitative analyzer combining a high-performance liquid chromatograph and a mass spectrometer and having therebetween a chemical ionization mechanism as an interface.

The high-performance liquid chromatograph allows to analysis of any and all such specimens as nonvolatile substances, thermally instable substances, organic compounds and high-molecular compounds, as long as the specimens are soluble in solvents even if they are mixtures. The mass spectrometer, on the other hand, has been utilized in the fields of organic chemistry, pharmacology and biochemistry, as a highly sensitive analyzer yielding such information as molecular weight and structure of organic compounds, but they cannot separate and identify any specimens if they are mixtures.

It is customary in the related industries that to combine the high-performance liquid chromatograph (LC) which separates, by each component, the mixtures as specimens and the mass spectrometer (MS) which analyzes the respective compounds. However direct combination of these two is impossible because the high-performance liquid chromatograph is an equipment which treats liquids at atmospheric pressure while the mass spectrometer is a high vacuum apparatus. From this it follows that an interface is required between the high-performance liquid chromatograph and the mass spectrometer.

One of such interfaces is Atmospheric Pressure Chemical Ionization (APCI). FIG. 1 illustrates a scheme of an analyzer which combines the high-performance liquid chromatograph and a mass spectrometer and incorporates the Atmospheric Pressure Chemical Ionization interface. In the figure, LC symbolizes the high-performance liquid chromatograph, APCI, the atmospheric pressure chemical ionization interface and MS, the mass spectrometer.

In the LC portion the numeral 1 represents a solvent, the mobile phase; 2, a pump to force the mobile phase through the system at high pressure; 3, an injector to introduce the sample into the mobile phase; 4, a chromatographic column; and 5, an ultraviolet detector. The numeral 11 in the APCI portion indicates a nebulizer having a metal capillary 12 and a cartridge heater 13; 14, an atmospheric nebulizer space; 15, a vaporizer having a vaporizer space 16 as well as a cartridge heater 17. The numeral 18 in the same portion is a corona discharge needle electrode connected to a high-voltage power supply 19. In the same figure the numeral 20 represents an atmospheric pressure ionization chamber, 21 a primary electrode having a fine pore at its center, 22 an intermediate electrode having also a fine pore at its center, 23 a secondary electrode with a similar pore also at its center; drift current has been applied between said primary electrode 21 and secondary electrode 23. Vac. 1 shown by an arrow in the APCI portion is connected to a vacuum pump. In the MS portion the numeral 25 symbolizes a focus coil, 26 an ion collector, 27 an amplifier, and 28 a data processor. Vac. 2 shown by another arrow in the MS portion is connected to the vacuum pump.

In the LC portion of the analyzer shown in FIG. 1, the specimen to be analyzed is injected from the injector 3, and the solvent 1 is fed by the pump 2. The specimen dissolved in the solvent is separated for each constituent by the chromatographic column 4 and sent to the APCI portion via the ultraviolet detector 5.

In the APCI portion the specimen solution is rapidly heated by the cartridge heater 13 while it passes through the metal capillary 12 of the nebulizer 11, and then nebulized over the nebulizer space 14 under atmospheric pressure. This thermal mist or nebula migrates across the vaporizer space 16 while being heated by the cartridge heater 17 of the vaporizer 15 and made to be finer and finer by accelerated desolvation of its droplets before entering into the atmospheric pressure ionization chamber 20, in which the corona discharge of a needle electrode 18 under the high voltage as applied by the high-voltage power supply 19, will ionize first the solvent molecules occupying the most part of the nebula. The solvent ions repeatedly collide with the solvent and specimen molecules to ionize the latter eventually. These ions will be accelerated by the drift voltage as applied between the primary electrode 21 and the secondary electrode 23, leaving for the MS portion by way of the respective central fine pores of the primary electrode 21, intermediate electrode 22 and secondary electrode 23. Meanwhile the chamber between the primary electrode 21 and intermediate electrode 22 as well as that between this same electrode 22 and the secondary electrode 23 are respectively held at the stages of intermediate pressures by the vacuum pump Vac. 1, and the ions are accelerated by the drift voltage in these intermediate pressure chambers and then will be desolvated after having repeated collisions with neutral molecules. The molecules of small molecular weight thus desolvated will diffuse and be exhausted from the vacuum pump Vac. 1.

The ions which entered into the MS portion will undergo the mass dispersion by the magnetic field of the focus coil 25 and the applied voltage of the ion collector 26. The wavelength of the current flowing into the ion collector will be amplified by the amplifier 27, plotted and displayed as a graph by the data processor 28, thus enabling review of the data peculiar to the ions from the MS spectral and the intensity of the MS chromatogram peaks.

The inventor attempted to detect the ions having particular mass only by the detector ion collector 26 (referred to as "SIM": Selected Ion Monitoring) in the MS portion of the foregoing analyzer shown in FIG. 1 to have the SIM chromatogram through the data processor 28. At the same time a quantitative analysis was tried with the concentration of specimen ions to be obtained from the area of the chromatogram peaks. Since however the peak areas of the SIM chromatogram of the specimen ions differed at each measurement though the specimens themselves were the same, this analyzer could not be applied to the quantitative analysis because of the poor reproducibility.

The use of the APCI analyzer which combines the high-performance liquid chromatograph and mass spectrometer had been limited to the qualitative analyses relating, for instance, to the molecular weight and structure of organic compounds in specimens. The quantitative analyses with such an analyzer had long been desired earnestly, but we have so far had no report thereon even in the Analytical Abstracts 1980-3/1994.

SUMMARY OF THE INVENTION

This invention made to solve the foregoing problems provides an analyzer in which a high-performance liquid chromatograph and a mass spectrometer are linked by means of an atmospheric pressure chemical ionization interface, which can operate in a stable state over a prolonged time, is excellent in the reproducibility of the peak areas of the SIM chromatogram and allows us to perform a quantitative analyses.

In the study conducted to employ, for the quantitative analyses, the foregoing analyzer as shown in the FIG. 1, the inventor found the fact that the reproducibility of the SIM chromatogram peak areas depends upon the quality of the materials of the corona discharging needle electrode 18 for the ionization of specimens in the atmospheric pressure chemical ionization (APCI) interface portion. As a result of continued in-depth research, he could achieve the present invention finding optimal materials for the corona discharging electrode to be employed in this analyzer.

The quantitative analyzer wherein the high-performance liquid chromatograph and the mass spectrometer are linked together by the atmospheric pressure chemical ionization interface, to which this invention has been applied to solve the foregoing problems, is characterized in that a corona discharging electrode made from metal materials consisting of silver alloy, platinum alloy, stainless steel, tinned iron or non-plated iron has been provided in the atmospheric pressure ionization chamber of the atmospheric pressure chemical ionization interface.

Likewise the corona discharging needle electrode, for ionization of specimens, of the atmospheric pressure chemical ionization interface which, in application of this invention, combines the high-performance liquid chromatograph and mass spectrometer, is characterized in that it is made into needle form from metallic materials consisting of silver alloy, platinum alloy, stainless steel, tinned iron or non-plated iron.

Silver alloy, stainless steel, and non-plated iron are preferred as the metallic materials for the corona discharging electrode for the atmospheric pressure chemical ionization interface.

More preferably, the above-mentioned silver alloy should contain silver as its primary component, and copper as auxiliary constituent.

DETAILED DESCRIPTION OF THE INVENTION

Figure 1:
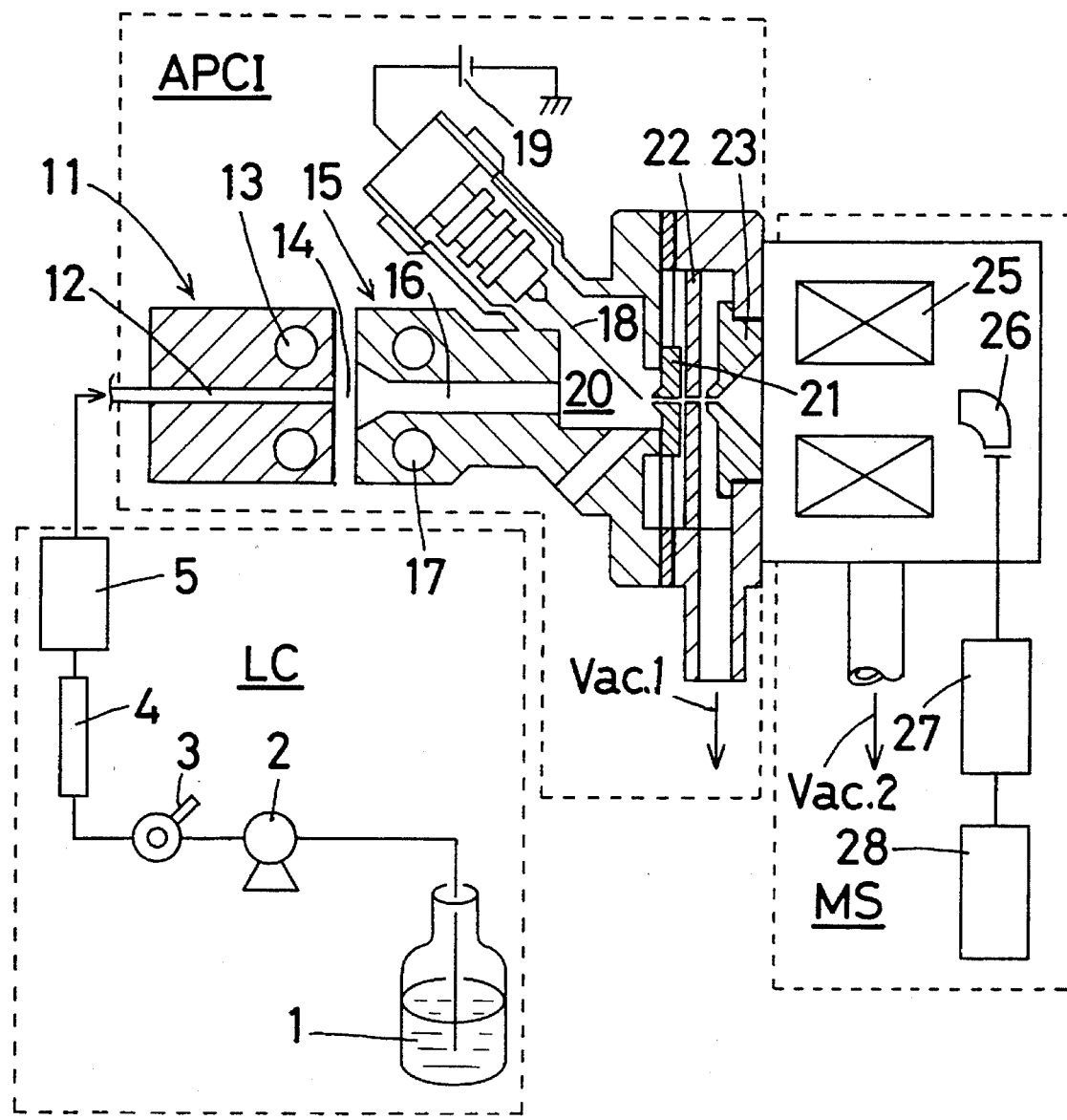
FIG. 1 is a schematic representation of an analyzer combining, by an interface of an atmospheric pressure chemical ionization, a high-performance liquid chromatograph and a mass spectrometer.

Tentatively manufactured were corona discharging needle electrodes from a wide variety of raw materials, which were mounted on an existing analyzer that linked, as schematically shown in FIG. 1, the high-performance liquid chromatograph and the mass spectrometer by and through the atmospheric pressure chemical ionization interface. Both stability and reproducibility were investigated of the chromatogram peak areas through quantitative analyses of the methanol solution of butylated hydroxytoluene. The analyzer employed in effect was Hitachi's LC/MS System Model M-1200H. Use of Japanese Industrial Standard (JIS) S3008 needle for cotton thread (referred to as "cotton needle") No. 5 is recommended as a referential corona discharge needle electrode.

Types of Corona Discharge Needle Electrodes

Referential Standard Needle A (Ni plated Fe): The cotton needle No.5 according to JIS S3008 as such, 0.84 mm in thickness, 45.5 mm in length, electro-nickeled iron. Only the eye of the needle has been gilded.

Trial Needle B (Ni-Au plated iron): This is an electrogilded cotton needle No. 5 (already nickeled) according to JIS S3008.

Trial Needle C (Au-plated Fe): Electrogilded cotton needle No. 5, JIS S3008 before being nickeled.

Trial Needle D (Ag-plated Fe): Silvered cotton needle, JIS S3008 No. 5 before being nickeled.

Trial Needle E (Sn-plated Fe): Electrotinned cotton needle No. 5 by JIS S3008 before being nickeled.

Trial Needle F (Cd-plated Fe): This is a cotton needle No.5, JIS S3008 chromate filmed and Cd-electroplated before being nickeled.

Trial Needle G (Pb-plated Fe): Pb-electroplated cotton needle No.5, JIS S3008 before being nickeled.

Trial Needle H (non-plated Fe): This is a cotton needle No.5, JIS S3008 before being nickeled.

Trial Needle I (14-Au): A wire of 14 carats fine gold (containing 58.5% or more gold, palladium and others) is cut off, ground into needle-like shape by a grinder, polished with sand paper, and then finished into the geometrical shape similar to the JIS S3008 cotton needle No. 5.

Trial Needle J (Ag-alloy): A wire of silver alloy (silver 95%, copper 5%) is cut off, ground into needle-like shape by a grinder, polished with sand paper, and then finished into the geometrical shape similar to the JIS S3008 cotton needle No. 5.

Trial Needle K (Pt-alloy): A wire of platinum alloy (platinum 90%, palladium 5%, copper 5%) is cut off, ground into needle-like shape by a grinder, polished with sand paper, and then finished into the geometrical shape similar to the JIS S3008 cotton needle No. 5.

Trial Needle L (stainless steel): A wire of stainless steel is cut off, ground into needle-like shape by a grinder, polished with sand paper, and then finished into the geometrical shape similar to the JIS S3008 cotton needle No. 5.

Trial Needle M (Cu): A copper wire is cut off, ground into needle-like shape by a grinder, polished with sand paper, and then finished into the geometrical shape similar to the JIS S3008 cotton needle No. 5.

Trial Needle N (18-Au): A wire of 18 carats fine gold (containing 75% or more gold, besides that, containing copper, zinc and lead) is cut off, ground into needle-like shape by a grinder, polished with sand paper, and then finished into the geometrical shape similar to the JIS S3008 cotton needle No. 5.

The following experiments were performed repeatedly by mounting, on the analyzer as shown in FIG. 1, the above wide variety of corona discharging needle electrodes 18 alternately one after another.

Butylated hydroxytoluene ($C_{15}H_{24}O$, molecular weight: 220.34) is dissolved, as reagent, into methanol as special grade chemical to prepare 5 ppm of solution. Onto the chromatographic column 4 of the high-performance liquid chromatograph LC, mounted is TSK-GEL ODS 80 TS, 15 cm×6 mm $\phi$ (TOSOH, Japan), and the temperature is maintained at room temperature. Methanol is added to the solvent 1, the mobile phase, and the flow rate is maintained at 1 ml/min by means of the pump 2. The ultraviolet detector is set at 280 nm of wavelength and 0.001 AUFS of sensitivity.

The atmospheric pressure chemical ionization (APCI) interface and the mass spectrometer MS were set as follows: the measurement mode was set negative, the measuring method set to selected ion monitoring (M/Z 219), the drift voltage applied between the primary electrode 21 and secondary one 23 to 30 V, the voltage of the multiplier, output of the amplifier 27 to 1800 V, the voltage of the corona discharging needle electrode 18 to be applied from the high-voltage power supply 19 to 2700 V, the temperature of the nebulizer 11 to be heated by the cartridge heater 13 to 200° C., the temperature of the vaporizer 15 to be heated by the cartridge heater 17 to 400° C., the temperature of the fine pore of the primary electrode 21 (aperture heater) to 120° C., and finally SIMSUM to 1.

This setting allowed us to evaluate the operating stability of the equipment as described in the following I to III.

I. Quantitative Reproducibility 1 to 2 Hours after the Start Up of the Equipment The equipment was activated. An hour after the start of the corona discharging by the needle electrode 18, specimen of 5 ppm butylated hydroxytoluene solution, 10 μl (actual volume of butylated hydroxytoluene: 50 ng) was injected from the injector 3, and separated by the chromatographic column 4. The butylated hydroxytoluene was thus determined to have the peak area. The time required for the butylated hydroxytoluene to eluate was about 4.5 minutes. The operation was repeated 7 times respectively (about one hour of measuring for one time), and the relative standard deviation was calculated from the value of the peak area thus obtained. Table 1 summarizes the results.

after 7 times of SIM separation and determination. Then from this area the relative standard deviation was calculated. Table 2 recapitulates the results of this experiment.

TABLE 1

| | Needle-type | | | | | | | | | | | | | |
| --- | --- | --- | --- | --- | --- | --- | --- | --- | --- | --- | --- | --- | --- | --- |
| Material | A Ni-plated Fe | B Ni-Au plated Fe | C Au-plated Fe | D Ag-plated Fe | E Sn-plated Fe | F Cd-plated Fe | G Pb-plated Fe | H Non-Plated Fe | I 14-Au | J Ag-alloy | K Pt-alloy | L Stain-less steel | M Cu | N 18-Au |
| 1 | 48001 | 33365 | 48153 | 43821 | 47207 | 43869 | 47378 | 62088 | 39965 | 50190 | 51392 | 54113 | 29100 | the |
| 2 | 48812 | 34351 | 48787 | 41850 | 46926 | 43354 | 49541 | 63652 | 42644 | 50872 | 49444 | 54324 | 27028 | needle |
| 3 | 52556 | 35564 | 47803 | 41572 | 48803 | 45236 | 47093 | 61750 | 41184 | 49568 | 49789 | 53271 | 26716 | was bent |
| 4 | 51202 | 35674 | 50642 | 40359 | 47503 | 42826 | 46473 | 61451 | 40641 | 50499 | 49302 | 53671 | 26745 | by dis- |
| 5 | 49347 | 35767 | 49503 | 40251 | 48113 | 43858 | 47501 | 62372 | 42576 | 50000 | 48608 | 54283 | 16415 | charge, |
| 6 | 50474 | 32639 | 49807 | 41235 | 47915 | 44965 | 47565 | 62292 | 42948 | 50204 | 48010 | 55265 | 16471 | unable |
| 7 | 50729 | 31928 | 51008 | 40527 | 49038 | 43396 | 47420 | 63042 | 42629 | 51061 | 49383 | 52726 | 24650 | to |
| Average | 50160 | 34184 | 49386 | 41374 | 47930 | 43929 | 47567 | 62378 | 41798 | 50342 | 49418 | 53950 | 23875 | continue |
| Dispersion | 1549 | 1571 | 1210 | 1244 | 789 | 878 | 947 | 754 | 1184 | 513 | 1056 | 821 | 5238 | |
| Standard deviation | 3.1 | 4.6 | 2.5 | 3.0 | 1.6 | 2.0 | 2.0 | 1.2 | 2.8 | 1.0 | 2.1 | 1.5 | 22 | |

II. Quantitative Reproducibility 5 to 6 Hours after the Start Up of the Equipment Five hours after the start of the corona discharge by the needle electrode 18, the same operation was performed in the same manner as one hour after the start up of the above-mentioned corona discharge to obtain the peak area

TABLE 2

| | Needle-type | | | | | | | | | | | | | |
| --- | --- | --- | --- | --- | --- | --- | --- | --- | --- | --- | --- | --- | --- | --- |
| Material | A Ni-plated Fe | B Ni-Au plated Fe | C Au-plated Fe | D Ag-plated Fe | E Sn-plated Fe | F Cd-plated Fe | G Pb-plated Fe | H Non-Plated Fe | I 14-Au | J Ag-alloy | K Pt-alloy | L Stain-less steel | M Cu | N 18-Au |
| 1 | 53565 | 31861 | 52712 | 47943 | 45919 | 47044 | dis- | 64118 | 43738 | 51756 | 52954 | 55371 | dis- | |
| 2 | 53282 | 33689 | 52447 | 45618 | 44999 | 47370 | con- | 63116 | 43742 | 49539 | 51354 | 54770 | continued | |
| 3 | 55536 | 34691 | 52772 | 45180 | 44987 | 47820 | tinued | 64657 | 43239 | 51070 | 51643 | 55618 | due to | |
| 4 | 53714 | 36726 | 53395 | 47361 | 45611 | 47169 | due to | 62665 | 45511 | 51328 | 51816 | 54430 | the bad | |
| 5 | 55125 | 37756 | 55225 | 45992 | 44953 | 45524 | foul | 63248 | 43607 | 49949 | 49597 | 54742 | result | |
| 6 | 56594 | 39413 | 53577 | 46290 | 44992 | 45344 | smell | 62759 | 44585 | 51576 | 48874 | 54842 | in | |
| 7 | 54717 | 39605 | 54214 | 47667 | 44815 | 47504 | | 62299 | 46662 | 50497 | 49607 | 58389 | Table 1 | |

TABLE 2-continued

| Material | Needle-type | | | | | | | | | | | | |
|---|---|---|---|---|---|---|---|---|---|---|---|---|---|
| | A Ni-plated Fe | B Ni-Au plated Fe | C Au-plated Fe | D Ag-plated Fe | E Sn-plated Fe | F Cd-plated Fe | G Pb-plated Fe | H Non-Plated Fe | I 14-Au | J Ag-alloy | K Pt-alloy | L Stainless steel | M Cu | N 18-Au |
| Average | 54648 | 36249 | 53477 | 46579 | 45182 | 46825 | | 63266 | 44441 | 50816 | 50835 | 55452 | | |
| Dispersion | 1205 | 2944 | 980 | 1077 | 413 | 983 | | 840 | 1240 | 844 | 1487 | 1357 | | |
| Standard deviation | 2.2 | 8.1 | 1.8 | 2.3 | 0.9 | 2.1 | | 1.3 | 2.8 | 1.7 | 2.9 | 2.4 | | |

III. Evaluation of the Quantitative Reproducibility

The analyzer suggests us about 8 hours of continuous use. Based on the quantitatively evaluated values of butylated hydroxytoluene determined 7 times 1 to 2 and 5 to 6 hours after the start of the corona discharges respectively, the sum of their relative standard deviations (N= 14) was calculated. The results of this calculation are shown in Table 3 as indices representing the reproducibility of the quantitative analyses.

TABLE 3

| Material | Needle-type | | | | |
|---|---|---|---|---|---|
| | A Ni-plated Fe | B Ni-Au plated Fe | C Au-plated Fe | D Ag-plated Fe | E Sn-plated Fe |
| Average 14 times | 52404 | 35216 | 51432 | 43976 | 46556 |
| Dispersion | 2683 | 2507 | 2372 | 2923 | 1549 |
| Standard deviation | 5.1 | 7.1 | 4.6 | 6.6 | 3.3 |
| Evaluation | Unfit for Q.A. | Unfit for Q.A. | Unfit for Q.A. | Unfit for Q.A. | Fit for Q.A. |

| | F Cd-plated Fe | G Pb-plated Fe | H Non-plated Fe | I 14-Au | J Ag-alloy |
|---|---|---|---|---|---|
| Average 14 times | 45376 | | 62822 | 43119 | 50579 |
| Dispersion | 1750 | | 895 | 1799 | 715 |
| Standard deviation | 3.9 | | 1.4 | 4.2 | 1.4 |
| Evaluation | Unfit for Q.A. | Unfit for needle electrode | Excellent for Q.A. | Unfit for Q.A. | Excellent for Q.A. |

| | K Pt-alloy | L Stainless steel | M Cu | N 18-Au |
|---|---|---|---|---|
| Average 14 times | 50127 | 54701 | | |
| Dispersion | 1440 | 1329 | | |
| Standard deviation | 2.9 | 2.4 | | |
| Evaluation | Good for Q.A. | Excellent for Q.A. | Unfit for Q.A. | Unfit |

Q.A. = Quantitative Analysis

The relative merits of the corona discharging needle electrodes, by their type, were evaluated with the total relative standard deviations as indices as shown in Table 3.

As a result it turned out that when the trial needles E (Sn-plated Fe), H (non-plated Fe), J (Ag-alloy), K (Pt-alloy), and L (stainless steel) are employed, the total standard deviations are small enough, that the peak areas of SIM chromatogram of butylated hydroxytoluene have been stably reproduced and that these needles can safely be employed in the quantitative analyses. It is clear that the non-plated needles as a whole are better, the sole plated needle electrode usable in quantitative analyses being the trial needle E made from tinned iron. As for the non-plated iron trial needle H, silver-alloy trial needle J and stainless steel trial needle L, they are practically useful—and preferable because they all present small enough total relative standard deviations and are available at comparatively modest prices.

For the referential standard needle A (Ni-plated Fe), the trial needles B (Ni-Au plated Fe), C (gilded Fe), D (Ag-plated Fe), F (Cd-plated Fe), and I (14-Au), their total relative standard deviations are large and the peak areas are instable of the SIM chromatogram of butylated hydroxytoluene. They manifested themselves to be inadequate for exacting quantitative analyses. The trial needle M (Cu), with its standard deviations, calculated over 7 times, of the peak areas of SIM chromatogram in the measurement of quantitative reproducibility 1 to 2 hours after the start of the equipment under experiment I, was estimated to be unavailable in any quantitative analyses without necessity to measure the quantitative reproducibility 5 to 6 hours after the start of the equipment under II.

The trial needle N (18-Au) was bent down by the shock of the corona discharge, which did not allow for any subsequent tests. Ever since the quantitative reproducibility was being measured of the trial needle G (Pb-plated Fe) 1 to 2 hours after the start of the equipment under the experiment I, it began to give out foul smell thus compelling us to drop the measurement of quantitative reproducibility 5 to 6 hours after the start of the equipment under II. The trial needle N of gold 18 carats fine and G of Pb-plated iron turned out to be inappropriate as corona discharging needle electrodes for the interface of the atmospheric pressure chemical ionization, to say nothing of whether they be available for quantitative analyses.

As has thus far been described in detail, in the quantitative analyzer according to this invention which links, through the atmospheric pressure chemical ionization interface, the high-performance liquid chromatograph and mass spectrometer, the corona discharging needle electrodes for ionization of specimens could be optimized, allowing thus to stabilize the reaction of the ion molecules due to the corona discharge and therefore to measure the chromatogram peak areas of the specimens as separated by the high-performance liquid chromatograph with excellent reproducibility. As a consequence not only such quantitative analyses with this type of analyzer, desired eagerly for a long time, but remained impossible, has become practical, but also its quantitative analyses enjoy an extremely high reliability.

What is claimed is:

1. A quantitative analyzing apparatus comprising: a high-performance liquid chromatograph, a mass spectrometer, and an atmospheric pressure chemical ionization interface for linking the liquid chromatograph to the mass spectrometer, wherein the interface includes an ionization chamber housing a corona discharge electrode comprised of a material selected from group consisting of a silver alloy and a non-plated iron.

2. The apparatus of claim 1, wherein said corona discharge electrode is comprised of said silver alloy.

3. The apparatus of claim 1, wherein said corona discharge electrode is comprised of said non-plated iron.

4. The apparatus of claim 1, wherein said corona discharge electrode is comprised of said silver alloy, said silver alloy containing silver as a primary component and copper as an auxiliary component.

* * * * *